(12) United States Patent
Gibson et al.

(10) Patent No.: US 9,492,591 B2
(45) Date of Patent: Nov. 15, 2016

(54) BONE GRAFT SYSTEM (75) Inventors: Iain Ronald Gibson, Aberdeen (GB); Janet Mabel Scott Skakle, Aberdeen (GB); Jordan Christopher Conway, Aberdeen (GB); Basil Annaz, Aberdeen (GB)

(73) Assignee: SIRAKOSS LIMITED, Scotland ( * ) Notice: Subject to any disclaimer, the term of this patent is extended or adjusted under 35 U.S.C. 154(b) by 0 days.

(21) Appl. No.: 13/806,243

(22) PCT Filed: Jun. 22, 2011

(86) PCT No.: PCT/GB2011/000939
§ 371 (c)(1),
(2), (4) Date: Dec. 21, 2012

(87) PCT Pub. No.: WO2011/161409
PCT Pub. Date: Dec. 29, 2011

(65) Prior Publication Data
US 2013/0095183 A1    Apr. 18, 2013

(30) Foreign Application Priority Data
Jun. 25, 2010    (GB) .................................. 1010761.3

(51) Int. Cl.
*A61L 27/46*    (2006.01)
*A61L 27/42*    (2006.01)
*A61L 27/52*    (2006.01)

(52) U.S. Cl.
CPC .............. *A61L 27/46* (2013.01); *A61L 27/425* (2013.01); *A61L 27/52* (2013.01); *A61L 2430/02* (2013.01)

(58) Field of Classification Search
CPC ............................ A61L 27/425; A61L 27/52
See application file for complete search history.

(56) References Cited

U.S. PATENT DOCUMENTS

| | | | |
|---|---|---|---|
| 6,312,468 B1 * | 11/2001 | Best .................. | A61L 27/12 106/462 |
| 8,288,344 B2 | 10/2012 | DePaula | |
| 2007/0059379 A1 * | 3/2007 | Gerber ................. | 424/602 |
| 2008/0152723 A9 | 6/2008 | Gerber | |
| 2009/0030089 A1 | 1/2009 | Sayer et al. | |
| 2009/0130230 A1 * | 5/2009 | Stanley, Sr. ........ | A61K 33/00 424/677 |
| 2011/0237552 A1 * | 9/2011 | Heinemann ........ | A61L 27/34 514/108 |

FOREIGN PATENT DOCUMENTS

| | | | | |
|---|---|---|---|---|
| AG | 202006013761 U | 12/2006 | | |
| DE | WO 2010029150 A2 * | 3/2010 | ............ | A61L 27/34 |
| EP | 1 584 338 | 10/2005 | | |
| JP | 2004-283439 | 10/2004 | | |
| WO | WO 9317976 A1 * | 9/1993 | ............ | A61L 27/10 |
| WO | WO 98/44964 | 10/1998 | | |
| WO | WO 2007/025698 A3 | 3/2007 | | |
| WO | 2007/045954 | 4/2007 | | |
| WO | WO 2010/29150 | 3/2010 | | |
| WO | WO 2010029150 A2 * | 3/2010 | ............ | A61L 27/34 |
| WO | WO 2010/079316 | 7/2010 | | |

OTHER PUBLICATIONS

Dorozhkin, S.V.; Dorozhkina, E.I.; Oktar, F.N.; Salman, S. "A Simplified Preparation Method of Silicon-Substituted Calcium Phosphates According to Green Chemistry Principles" Key Engineering Materials, 2007, vols. 330-332, 55-58.*

Shirosaki, Y.; Botelho, C.M.; Lopes, M.A.; Santos, J.D. "Synthesis and Characterization of Chitosan-Silicate Hydrogel as Resorbable Vehicle for Bonelike® Bone Graft" J. Nanosci. Nanotech. 2009, 9, 3714-3719.*

Kortesuo, P. et al., "Sol-gel-processed sintered silica xerogel as a carrier in controlled drug delivery", J Biomed Mater Res. (1999) 44(2):162-167.

Daculsi, G. et al., "Developments in injectable multiphasic biomaterials. The performance of microporous biphasic calcium phosphate granule and hydrogels," Journal of Material Science: Material Medicine (2010) 21:855-861 (Epub Nov. 1, 2009.

Gough, J.E. et al., "Nodule formation and mineralisation of human primary osteblast cultured on a porous bioactive glass scaffold," *Biomaterials* (2004) 25:2039-2046.

Guth, K. et al., "Silicon dissolution from micropourous silicon substituted hydroxyapatite and its effect on osteoblast behavior," *Key Engineering Materials* (2006) 309-311:117-120.

Shirosaki, Y. et al., "Synthesis and characterization of chitosan-silicate hyrdrogel as resorbable vehicle for bonelike-bone graft," *Journal of Nanoscience and Nanotechnology* (2009) 9(6):3714-3719 (Abstract).

Weinand, C. et al., "Hydrogel-β-TCP scaffolds and stem cells for tissue engineering bone," Bone (2006) 38(4): 555-563 (Epub Dec. 20, 2005)

Xynos, I. et al., "Ionic products of bioactive glass dissolution increase proliferation of human osteoblasts and induce insulin-like growth factor II mRNA expression and protein synthesis," Biochemical and Biophysical Research Communications (2000) 276(2):461-465.

Search Report dated Oct. 28, 2010 from Great Britain patent application No. GB1010761.3 (7 pages).

(Continued)

*Primary Examiner* — Brian-Yong Kwon
*Assistant Examiner* — Andrew S Rosenthal
(74) *Attorney, Agent, or Firm* — Andrus Intellectual Property Law, LLP (57) ABSTRACT

The bone graft system comprises a solid inorganic component, which is bone graft material, and a hydrogel. The hydrogel contains >2 ppm of silicon ions, calculated as parts by weight of Si per million of the aqueous component of the hydrogel. Preferably, the solid inorganic component comprises hydroxyapatite or a silicon-containing hydroxyapatite, and may be a silicon-containing hydroxyapatite having a Ca/P ratio in the range 2.05 to 2.55 and a Ca/(P+Si) molar ratio less than 1.66. Bone healing is promoted by delivery of silicon ion release from the hydrogel and by the solid inorganic component stimulating cell behavior.

22 Claims, 2 Drawing Sheets

(56) References Cited

OTHER PUBLICATIONS

Brinker C.J., "Hydrolysis and condensation of silicates: Effects on structure," (1988) Journal of Non-Crystalline Solids 100:31-50.

Fidalgo, A. et al., "Chemical tailoring of porous silica xerogels: Local structure by vibrational spectroscopy," (2004) 10:392-398.

Shirosaki, Y. et al., "In vitro cytocompatibility of MG63 cells on chitosan-organosiloxane hybrid membranes," (2005) Biomaterials 26:485-493.

Likorish, D. et al., "Collagen-hydroxyapatite composite prepared by biomimetic process," (2003) J. Biomed Mater Res 68A: 19-27.

* cited by examiner

BONE GRAFT SYSTEM

TECHNICAL FIELD

The present invention relates to bone graft systems, in particular to bone graft systems which include a gel component.

BACKGROUND OF THE INVENTION

Due to disease or trauma, surgeons need to replace bone tissue. They can use bone grafts (autografts or allografts) or synthetic materials to replace bone during surgery. Amongst the types of synthetic materials used to replace bone, surgeons use metals (e.g. stainless steel hip or knee implants), polymers (e.g. polyethylene in acetabular cups), ceramics (e.g. hydroxyapatite as a macroporous bone graft) or inorganic-organic composites (e.g. hydroxyapatite-poly(lactic acid) composites for fixation plates). Many of these synthetic bone replacement materials are not resorbable in the body (within a period appropriate to the healing period) and do not stimulate the formation of new bone around or within the implant.

Materials which have generated particular interest include synthetic calcium phosphate (CaP) bone graft substitutes. Materials of this type can delivered to the intended site of bone regeneration in the form of a delivery system comprising granules incorporated in an organic polymer gel as a carrier, for example a hydrogel (e.g. carboxymethyl cellulose, CMC, based hydrogel).

Such delivery systems are designed to improve the handling of CaP granules, and to ease placement of the bone graft in the surgical site. The carrier is quickly resorbed or dissolved in the body (typically within 3 to 30 days) to expose the CaP granules for graft-bone interaction.

The carrier used in these delivery systems is selected for its handling characteristics, its safety, and its ability to be quickly resorbed or dissolved in the body. Typically, the polymers in the carrier chosen are natural polymers (e.g. collagen or gelatin), or approved synthetic polymers such as carboxymethyl cellulose (CMC). The carrier does not play an active role in bone repair (for example, in the case of carboxymethyl cellulose, hydroxylpropyl methylcellulose or glycerol). The carrier acts as a handling aid, carrying the active CaP granules to the site for bone regeneration and then dissolving or being resorbed.

The carriers referred to herein act as gels. In general terms, the definition of a gel is a jelly-like substance consisting of, by weight, mostly a liquid, but which exists as a solid, exhibiting no flow in the steady state. In a gel, polymer chains (the "solid phase" of the gel) exist in the "liquid phase" of the gel and interact via chemical cross-linking (e.g. covalent bonding) and/or physical interactions (e.g. hydrogen bonding or Van der Waals bonding) between the polymer chains. It is these interactions between the polymer chains that contributes to the structure and viscoelasticity of the gel.

A hydrogel is a specific type of gel in which water makes up the liquid phase. Typically the solid phase (i.e. the polymer) is dispersed in water under the conditions appropriate for the specific hydrogel to be formed. For example, acid soluble type I collagen can be dispersed (dissolved) in water under dilute acidic conditions (e.g. acetic acid) and will form a gel upon warming to 37° C. (with or without pre-neutralisation of the solution with a suitable base).

As gel formation (gelation) only occurs under particular conditions, a mixture of the ingredients of the gel may not actually be in the form of a gel. Such a solution which has not undergone gelation is referred to herein as a "gel solution". A gel solution undergoes gelation to form a gel.

Silicon has been shown to play an important role in bone formation and in bone metabolism. Work has therefore been done attempting to form silicon-containing bone graft materials. The synthesis of a silicon-substituted hydroxyapatite material is described in WO 98/08773 and corresponding U.S. Pat. No. 6,312,468. Although these materials have been shown to accelerate the rate of bone healing in animal studies and in human clinical studies, these silicon substituted materials are still very insoluble.

Some synthetic CaP biomaterials incorporate silicon ions as silicates. Examples include bioactive glasses, apatite-wollastonite glass ceramics, silicon-substituted hydroxyapatite and silicon-substituted tricalcium phosphate. Guth et al., *Key Engineering Materials*, Bioceramics, 2006, 309-311, pages 117-120 suggest that a low level of silicon is released from silicon substituted hydroxyapatite into tissue culture medium. A maximum of around 0.5 µg/ml silicon was reported. Gough et al., *Biomaterials*, 2004, 25, pages 2039-2046 report a foamed silicon-containing bioactive glass which was incubated for 24 hours in culture medium. Cells were cultured in the resulting conditioned medium neat, or diluted 1:1 or 1:4 with the culture medium. Silicon release was reported as 230 µg/ml in the neat eluate, 120 µg/ml when diluted 1:1 in culture medium and 47 µg/ml when diluted 1:4 in culture medium. Xynos et al., Biochem. Biophys. Res. Commun., 2000, 276, pages 461-465 report a bioactive glass Bioglass 45S5 containing 45% $SiO_2$ w/w. 1% w/v particulate of this glass, 710-300 µm diameter, was incubated in Dulbecco's modified eagle medium (DMEM) for 24 hours at 37° C. and remaining particulate removed by filtration. The medium was then supplemented with 10% fetal bovine serum, 2 mM 1-glutamine, 50 U/ml penicillin G, 50 µg/ml streptomycin B and 0.3 µg/ml amphotericin B at 37° C., in 95% air humidity and 5% $CO_2$. The elementary content of calcium, silicon, phosphorus and sodium in this solution was determined by inductively coupled plasma analysis. Xynos et al report a content of 0.19 ppm+/−0.01 Si in the control DMEM, and 16.58 ppm+/−1.78 in the Bioglass 45S5-conditioned DMEM.

PCT/GB2009/002954 (not yet published) describes a more soluble silicate-substituted calcium phosphate hydroxyapatite, having a Ca/P ratio in the range 2.05 to 2.55 and a Ca/(P+Si) molar ratio less than 1.66. These silicon-substituted hydroxyapatites exhibit a high level of solubility compared to hydroxyapatite ceramics or previously reported silicon-substituted hydroxyapatite ceramics, and release high levels of silicon on soaking in solution. For example, approximately 10-100 times as much silicon is released from the silicate-substituted hydroxyapatites described in PCT/GB2009/002954 compared to previously reported silicon-substituted hydroxyapatites.

DISCLOSURE OF THE INVENTION

For clarification, the incorporation of silicon into a material is referred to by those skilled in the art as silicon or silicate substitution. These terms are used interchangeably. Similarly, "silicon-containing", "silicate-containing", "silicon-substituted" and "silicate-substituted" are used interchangeably. Where the term "silicon ion" is used, this means silicate ion, including 'silicic acid' anion, that is, $SiO_4^{4-}$, as well as silicate ions which can exist in solution such as dimeric, trimeric or oligomeric forms of silicic acid anion.

In one aspect, the present invention provides a bone graft system comprising a solid inorganic component, which is a bone graft material; and a hydrogel, wherein the hydrogel contains >2 ppm of silicon ions, calculated as parts by weight of Si per million of the aqueous component of the hydrogel.

Herein, 'parts per million' (ppm) of ions in the hydrogel refers to parts per million with respect to the aqueous component of the hydrogel. For most hydrogels, the aqueous component is 90 to 99 wt % of the hydrogel.

Silicon or silicate ion concentration is calculated as parts by weight of Si per million of the aqueous component of the hydrogel. In expressing the amount of silicon ions in this manner, the silicon which may be present in another form in the composition, for example in the bone graft material, is ignored.

In the calculation, only the weight of silicon itself is used. That is, if an $SiO_4^{4-}$ ion is present, the weight of one atom of Si is used rather than one atom of Si plus 4 atoms of O.

The bone graft system of the present invention provides advantageous bone healing properties by delivering effective ions in two manners: by silicon ion release from the hydrogel, and by the solid inorganic component stimulating cell behaviour (for example through granule chemistry and/or morphology), Cells are thereby stimulated to produce new bone in what can be described as a 'multi-stage' bone repair process.

The importance of including silicon ions in the hydrogel (which acts as a carrier) is that the stimulatory activity of silicon in bone formation can be obtained directly from the hydrogel, rather than having to rely on the previous poorly soluble silicon-containing CaP biomaterials. This stimulatory activity is only achieved when significant, non-trace amounts of silicon ions are present in the hydrogel. Silicon ion levels of >2 ppm in the hydrogel have been found to be effective. Levels of >3 ppm are preferred. Particularly preferred are levels of ≥5 ppm.

The levels of silicon ions in the water (liquid phase) of the hydrogel are typically greater than or equal to 2 ppm and less than or equal to 2000 ppm, preferably greater than or equal to 5 ppm and less than or equal, to 1000 ppm. The hydrogel of the bone graft system of the present invention typically dissolves in the body in about 3 to 30 days. The level of silicon ions released locally at the implantation site depends on this degradation rate and also the nature of the implantation site, in terms of the rate of diffusion of fluids at that site. Daily release of silicon ions from the gel is caused by dissolution of the gel, and varies depending on the rate of dissolution and the amount of silicon ions contained in the gel. For example, a gel that contains 5 ppm of silicon ions and takes 10 days to dissolve can be said to provide a daily release of silicon of 0.5 ppm. Typical daily release of silicon ions from the gel may be between about 0.5 and 200 ppm, preferably between about 2 and 100 ppm.

In the present invention, the ratio (volume %) of the solid inorganic component, which is a bone graft material, to the hydrogel can be anywhere between 99:1 and 1:99. In preferred embodiments, the ratio is between 95:5 and 20:80. More preferably, it is between 90:10 and 50:50. Preferably, the bone graft system of the present invention is, by volume, greater than or equal to 50% solid inorganic component.

In some embodiments of the present invention, the ratio is between 50:50 and 80:20. In some embodiments, the ratio is between 70:30 and 80:20.

As the polymer carrier (hydrogel) of the bone graft delivery system dissolves, the silicon ions contained therein are released and can stimulate bone regeneration at the surgical site. Previous compositions have included a carrier purely as a handling improvement. Those carriers were chosen for their inability to interact with the body, and for their quick dissolution or resorbability.

Figure 1:
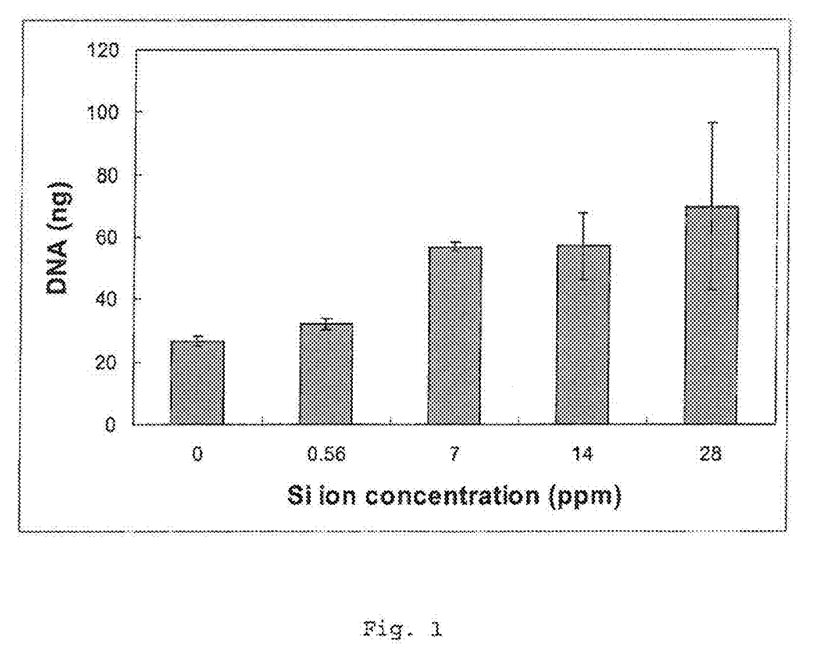
FIG. 1: Graph showing the effect of supplementing a cell culture medium, containing 10% FBS and various concentrations of silicon ions, with 0, 0.56, 7, 14 and 28 ppm silicon ions on the amount of DNA (ng) present in cell lysates after 7 days of culture.
Figure 2:
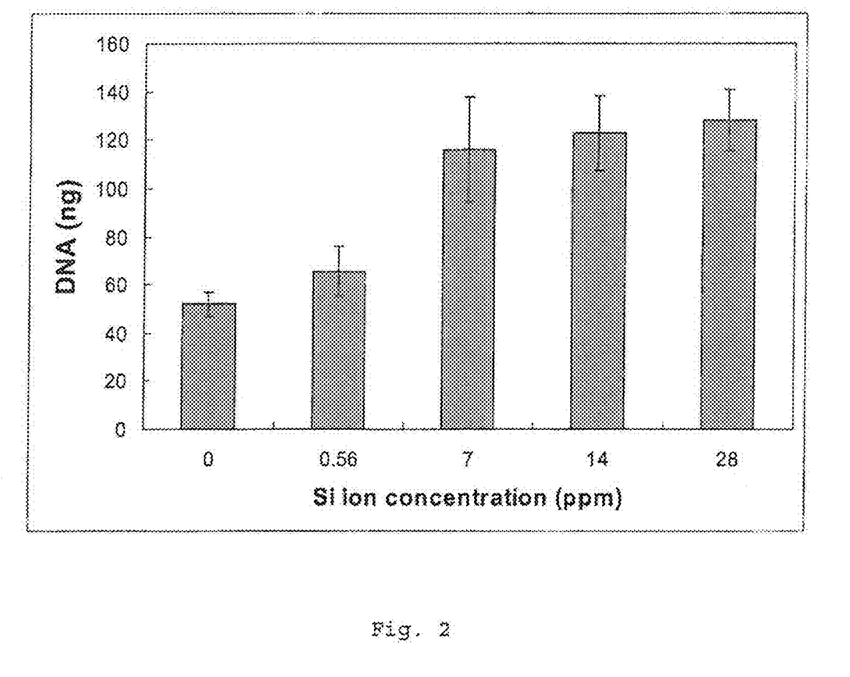
FIG. 2: Graph showing the effect of supplementing a cell culture medium, containing 10% FBS and various concentrations of silicon ions, with 0, 0.56, 7, 14 and 28 ppm silicon ions on the amount of DNA (ng) present in cell lysates after 14 days of culture.

The present inventors have found that silicon ions at an appropriate concentration have a stimulatory role on bone cell (osteoblast) proliferation, differentiation, protein expression and gene expression in vitro. For example, primary human osteoblast cells were grown in culture in a cell culture medium containing 10% FBS and various concentrations of silicon ions (measured in ppm, and added to the medium using a sodium silicate solution) of 0, 0.56, 7.0, 14.0, and 28.0 ppm. Cells were cultured for 7 or 14 days, and the total amount of DNA in cell lysates was quantified using a commercial assay.

FIGS. 1 and 2 show the changes in total DNA at 7 and 14 days of culture respectively for these different silicon ion concentrations. Levels of 7-28 ppm of silicon ions resulted in large increases in DNA compared with the control (0 ppm silicon ions) at both time points, and this result was indicative of a positive role of these silicon ion concentrations on the number of cells present, that is, on cell growth. This has implications in bone repair, as an increase in the number of cells can be associated with greater quantities of new bone matrix produced by these cells.

The bone graft systems and gels described herein can be sterilised using standard industry methods such as gamma irradiation.

Solid Inorganic Component

The solid inorganic component of the bone graft delivery system of the present invention is generally included in the form of granules or powder.

For example, the solid inorganic component may be included in the form of granules having diameter between 0.001 and 10 mm, more preferably between 0.5 and 5 mm, and most preferably between 1 and 2 mm. This diameter gives increased surface area of the solid inorganic component, increasing bone healing capabilities.

The solid inorganic component is in some embodiments present as particles distributed through the matrix of the hydrogel. The particles are held by the polymer matrix of the hydrogel.

The solid inorganic component may be synthetic or non-synthetic, such as allograft or DBM (Demineralised Bone Matrix). There may of course be more than one bone graft material present, each independently selected.

For example, the bone graft system of the present invention may include two solid inorganic components, one being synthetic and the other being non-synthetic.

Suitable solid inorganic components include biphasic calcium phosphate (BCP), calcium carbonate, hydroxyapatite, ion substituted hydroxyapatite, tricalcium phosphate, calcium sulphate, calcium silicate, octacalcium phosphate, amorphous calcium phosphate, brushite, monetite, tetracalcium phosphate, calcium pyrophosphate, bioglass, calcium silicate glass, calcium silicate-based glass, calcium phosphate glass, calcium phosphate-based glass, calcium silicate-based glass-ceramic, calcium phosphate-based glass-ceramic, bioactive glasses, bioactive glass-ceramics, biocompatible glasses, biocompatible glass-ceramics, alumina and zirconia.

An example biphasic calcium phosphate includes hydroxyapatite $(Ca_{10}(PO_4)_6(CO)_2)$ and β-tricalcium phosphate $(Ca_3(PO_2)_2)$. The ratio of inclusion of these components may vary. For example, the biphasic calcium phosphate may be 50% hydroxyapatite and 50% tricalcium phosphate. Other ratios can be used instead.

Suitable examples of silicon-containing glasses or glass ceramics include, but are not limited to, compositions based on the XO—Y$_2$O—SiO$_2$ or XO—Y$_2$—SiO$_2$—P$_2$O$_5$ systems, where X is typically Ca (calcium) and/or Mg (magnesium) and/or Sr (strontium), and Y is typically Na (sodium) and/or K (potassium). In these compositions, each K may be independently selected from the group consisting of Ca, Mg and Sr. Each Y may be independently selected from the group consisting of Na and K.

Suitable calcium silicate based compositions include crystalline calcium silicate phases, such as CaSiO$_3$ (wollastonite), or amorphous calcium silicate glass compositions in the CaO—SiO$_2$ system.

Preferred solid inorganic components include hydroxyapatite and silicon-containing hydroxyapatites.

An example hydroxyapatite is Ca$_{10}$(PO$_4$)$_6$(OH)$_2$. An example silicon-containing hydroxyapatite is Ca$_{9.85}$(PO$_4$)$_4$(SiO$_4$)$_2$)OH)$_y$, wherein y represents an amount of OH$^-$ ions present and is generally between 0 and 1. y is ideally 0, but reaction conditions can cause a variable amount of OH ions to be present (where some Si$_2$O$_7^{6-}$ is formed rather than SiO$_4^{4-}$).

A particularly preferable material for use as the solid inorganic component of the present bone graft systems is a silicon-containing hydroxyapatite having a Ca/P ratio in the range 2.05 to 2.55 and a Ca/(P+Si) molar ratio less than 1.66. Materials of this type are described in PCT/GB2009/002954. These materials are of improved solubility over other known hydroxyapatite materials.

Silicon-containing hydroxyapatites of this type soaked in a cell culture medium (0.5 g/50 ml) have been found to release 17 ppm of silicon ions after 1 hour of soaking.

Preferably, the silicon atom content of such a solid component is in the range of 2.9 to 6 wt %. In one embodiment, such solid component is represented by formula (I):

$$Ca_{10-\delta}(PO_4)_{6-x}(SiO_4)_x(OH)_{2-x} \qquad (I)$$

wherein 1.1≤x≤2.0, and

δ represents a Ca deficiency such that the Ca/(P+Si) molar ratio has a value less than 1.667.

Preferably, 1.2≤x≤2.0, more preferably 1.4≤x≤2.0, and most preferably 1.6≤x≤2.0. Generally, it is desirable that such solid component contains hydroxyl ions.

An example of such a material is Ca$_{9.85}$(PO$_4$)$_4$(SiO$_4$)$_2$(OH)$_y$, mentioned above.

Silicon-containing hydroxyapatites of these types have been found to exhibit a high level of solubility compared to hydroxyapatite ceramics or previously reported silicon-substituted hydroxyapatite ceramics, and release high levels of silicon on soaking in solution.

A higher silicon atom content of a silicon-containing hydroxyapatite is desirable to release a larger amount of silicon ions when the component is present in the hydrogel. In some embodiments, the silicon atom content is preferably at least 2.9 wt %, more preferably at least 3.5 wt %, and most preferably at least 5 wt %. In the silicon-substituted hydroxyapatites of the type described in PCT/GB2009/002954, these values are equivalent to a silicate (SiO$_4$) content of at least 9.5 wt %, at least 11.5 wt %, and at least 16 wt % respectively. The silicon atom content is preferably in the range 3.5 to 6 wt % (11.5 to 20 wt % silicate), and more preferably in the range 5 to 6 wt % (16 to 20 wt % silicate).

In the silicon-substituted hydroxyapatites of the type described in PCT/GB2009/002954, the molar ratio of calcium to phosphorus-containing ions (Ca/P ratio) is higher than that observed in stoichiometric hydroxyapatite (which is 10:6, or 1:0.6, or a Ca/P ratio of 1.67) or in prior art materials incorporating silicate in calcium phosphates. In one embodiment where the solid component of the present bone graft system is a silicon-substituted hydroxyapatite of the type described in PCT/GB2009/002954, the Ca/P molar ratio of that hydroxyapatite is at least 2.05. Preferably, the Ca/P molar ratio is at least 2.1, more preferably at least 2.2, and most preferably at least 2.3. The maximum Ca/P molar ratio is 2.55, preferably 2.5. Accordingly, the Ca/P molar ratio may be in the range 2.05 to 2.55, preferably 2.1 to 2.55, more preferably 2.2 to 2.5, or most preferably 2.3 to 2.5.

In the silicon-substituted hydroxyapatites of the type described in PCT/GB2009/002954, the molar ratio of Ca/(P+Si) is less than 1.66, preferably not more than 1.65, which is significantly lower than the Ca/(P+Si) molar ratio of 1.667 of other silicon-containing hydroxyapatite compositions. Preferably, the Ca/(P+Si) molar ratio is in the range 1.50 to 1.65, more preferably in the range 1.60 to 1.65, yet more preferably in the range 1.60 to 1.64.

Hydrogel

In the present invention, a hydrogel is used as a carrier. It may be of any suitable type, for example comprising a natural polymer such as collagen or gelatin, or a biologically compatible synthetic polymer such as carboxymethyl cellulose.

Preferred hydrogels include those with a polymer component which is carboxymethyl cellulose, collagen, gelatin, glycerol, hydroxypropylmethyl cellulose, or synthetic olefin or olefin oxide polymers. One example is an ethylene oxide/propylene oxide block copolymer (such as Pluronic® F 127 or F 68, BASF SE).

Typical carboxymethyl cellulose components are of medium or high viscosity. An example gel solution comprises 5% by weight carboxymethyl cellulose.

Some suitable gel solutions comprise 5 to 40% by weight, preferably 20 to 30% by weight, of an ethylene oxide/propylene oxide block copolymer such as Pluronic®F 127 or F 68, BASF SE. Other polymers, with different chain lengths, may also be used.

Hydrogels may also contain combinations of such components. For example, the hydrogel may contain both carboxymethyl cellulose and glycerol. Addition of glycerol has been found to improve the handling characteristics of a CMC hydrogel in the present invention.

An example gel solution contains 5% by weight carboxymethyl cellulose and 10% by weight glycerol.

Gel formation can be achieved by known methods. For example, a gel solution containing carboxymethyl cellulose may be heated to about 50° C. to dissolve the carboxymethyl cellulose, then cooled to room temperature to undergo gelation. A gel solution containing collagen may be aged at about 40° C. (e.g. 37° C.) overnight until gelation occurs. A gel solution containing a Pluronic® copolymer may be stirred at about 5° C. (e.g. 4° C.) overnight to dissolve the Pluronic® and then warmed to about 40° C. (e.g. 37° C.) overnight to allow gelation to occur. Alternatively, a gel solution containing Pluronic® can be formed at about 70° C. to 80° C., and then cooled to 20° C. to 40° C. to undergo geltation.

Silicon ions are held within the aqueous component of the hydrogel (that is, the liquid phase of the gel), such that on dissolution, degradation or resorption of the gel in vivo the silicon ions are released. Then, they can act to aid bone repair, healing etc.

This 'release on degradation' mechanism of ion delivery from the hydrogel is applicable to other ions that may be present in the hydrogel as well. Such optional further additives are discussed in more detail below.

The hydrogel may be formed separately, and the silicon ions later mixed with it to form the silicon-containing gel described above. A synthetic bone graft material may be used which, when mixed with an aqueous polymer phase (hydrogel), releases an appropriate level of silicon ions into the aqueous polymer phase (hydrogel).

Alternatively, a silicon ion source, which may also be a silicon-containing bone graft material such as those described herein (able to release appropriate levels of silicon ions in vitro), may be soaked in an aqueous solution to release the silicon ions. Then this silicon-containing aqueous solution can be used to make up the hydrogel.

Ionic Components in the Hydrogel

In the bone graft systems of the present invention, the hydrogel includes silicon ions. The silicon ions may be incorporated by any suitable method, such as mixing a hydrogel with a silicon-containing synthetic bone graft able to release silicon ions into the hydrogel, dissolving a silicon ion source in an aqueous solution and then using that aqueous solution to make up the hydrogel, or soaking a silicon-containing bone graft material, able to release silicon ions in vitro in an aqueous solution and then using that aqueous solution to make up the hydrogel.

The silicon ions may be incorporated by way of any suitable ionic silicon source. Several methods of incorporating the silicon ions from the silicon ion source into the hydrogel are discussed herein.

One way of incorporating silicon ions into a gel carrier is by direct release of the ions from a silicon ion source, either directly into the hydrogel or into an aqueous solution which is then used to make up the hydrogel. For example, a sodium silicate or calcium silicate can be used as the silicon ion source.

Where a silicate is used, various forms are suitable, such as (in the case of sodium silicates) $Na_4SiO_4$, $Na_2SiO_3$, $Na_2Si_2O_7$, $Na_2Si_3O_7$, hydrated forms of these sodium silicates, amorphous compositions of sodium silicate and so on.

A preferred silicate for use as a silicon ion source is $Na_2SiO_3$.

Where $Na_2SiO_3$ is used, a final concentration of between 5 and 2000 ppm in water can be obtained by dissolving between 0.0011 and 0.436 g of $Na_2SiO_3$; in 50 ml of water. This is shown in Example 7 (Table 1) below.

A sodium silicate such as $Na_2SiO_3$ may be dissolved in water to form a silicon-ion-containing solution, which is then used to make up a hydrogel.

Another example is the use of silicon-containing glasses or glass ceramics, or calcium silicate based compositions as the source of silicon ions.

Suitable examples of silicon-containing glasses or glass ceramics include, but are not limited to, compositions based on the $XO—Y_2O—SiO_2$ or $XO—Y_2O—SiO_2—P_2O_5$ systems, where X is typically Ca (calcium) and/or Mg (magnesium) and/or Sr (strontium), and Y is typically Na (sodium) and/or K (potassium). In these compositions, each X may be independently selected from the group consisting of Ca, Mg and Sr. Each Y may be independently selected from the group consisting of Na and K.

Suitable calcium silicate based compositions include crystalline calcium silicate phases, such as $CaSiO_3$ (wollastonite), or amorphous calcium silicate glass compositions in the $CaO—SiO_2$ system.

A preferable material for use as a silicon ion source is a silicon-containing hydroxyapatite having a Ca/P ratio in the range 2.05 to 2.55 and a Ca/(P+Si) molar ratio less than 1.66.

Materials of this type are described in PCT/GB2009/002954. These materials are of improved solubility over other known hydroxyapatite materials.

These materials, and their preferable characteristics, are as described above with regard to their inclusion as the solid component of the present bone graft systems.

Such materials can be soaked in water, releasing silicon ions into the water. The silicon-ion-containing solution thus produced can then be used to make up a hydrogel.

In some embodiments, further ions may be incorporated in the hydrogel, in particular calcium and/or phosphate ions. That is, the hydrogel may include silicon and calcium ions, silicon and phosphate ions, or silicon, calcium and phosphate ions.

Both calcium and phosphate ions are known to promote bone regeneration. It is well known to the skilled person that phosphate ions exist in many forms, not limited to $PO_4^{3-}$. Any form of phosphate ion may be included in the hydrogel of the present invention.

In addition, the hydrogel may include other components. The hydrogel may include ions which enhance bone healing response, and/or which exhibit an anti-bacterial effect, for example ions of strontium, magnesium, potassium, copper, cobalt, nickel, zinc, selenium, silver or fluorine.

In addition, the hydrogel may include active biomolecules such as growth factor proteins (such as bone morphogenic proteins), antibiotics (such as gentamicin) or other pharmaceutical drugs, cytokines or antibodies.

Methods

Another aspect of the present invention is a method of making a bone graft system, comprising the step of mixing a silicon ion source with a hydrogel.

In some embodiments, this method includes the further step of mixing a solid inorganic component, which is a bone graft material, with the hydrogel.

The silicon ion source is selected such that an appropriate level of silicon ions (as explained above) is released from it into the hydrogel. For example, a silicon-substituted calcium phosphate that is able to release >2 ppm (preferably >3 ppm, more preferably ≥5 ppm) of silicon ions in vitro can be used. Alternatively, silicon-containing glasses or glass ceramics, or calcium silicate based compositions, can be used as the silicon ion source in this method. Suitable silicon ion sources are discussed in more detail above.

In some embodiments of the present invention, the silicon ion source is not itself a bone graft material. Then, a solid inorganic component, which is a bone graft material, is also included in the silicon-containing gel to form a bone graft system according to the present invention.

In other embodiments, the silicon ion source is itself a bone graft material, and continues to act as such after it has released silicon ions into the hydrogel. The mixture can be used as a bone graft system as described herein without further alteration. Alternatively, further solid inorganic component (bone graft material) can be added to the mixture.

So, a solid inorganic component, which is the same as or different to the silicon ion source, and which is a bone graft material, can be added to the resulting mixture to form a bone graft system according to the present invention.

Another aspect of the present invention is a method of making a bone graft system, comprising the steps of (a) soaking or dissolving a suitable silicon ion source in an aqueous solution to form a solution comprising >2 ppm of silicon ions; (b) mixing the resulting aqueous solution with a polymer to form a gel solution; (c) allowing gelation of the gel solution to occur to form a hydrogel; and (d) mixing a solid inorganic component with the resulting hydrogel to make up the bone graft system.

As a further aspect of the present invention, there is provided a method of making a bone graft system, comprising the steps of (a) soaking or dissolving a suitable silicon ion source in an aqueous solution to form a solution comprising >2 ppm of silicon ions; (b) mixing the resulting aqueous solution with a polymer to form a gel solution; (c) mixing a solid inorganic component with the gel solution; and (d) allowing gelation of the gel solution to occur to form the bone graft system.

That is, gelation of the gel solution (aqueous mixture containing silicon ions and polymer) may occur before the solid inorganic component is added, or may occur after that component is added. As gelation occurs only under certain conditions, the time of gelation can be controlled to allow this variation.

In some embodiments, the silicon ion source used in step (a) is a silicon-containing bone graft material.

Preferably, the silicon ion source is able to release >2 ppm, preferably >3 ppm, more preferably ≥5 ppm, of silicon ions in vitro. The levels of silicon ions in the final polymer should be >2 ppm, preferably >3 ppm, more preferably ≥5 ppm.

The solid inorganic component mixed with the hydrogel may be the same as or similar to the silicon ion source soaked in the original aqueous solution, or it may be a different solid inorganic component. It is envisaged that a wide range of solid inorganic component/hydrogel combinations can be used in this method.

In some embodiments, the silicon ion source is a sodium silicate. Suitable silicon ion sources are discussed in more detail above. In some embodiments, the silicon ion source is $Na_2SiO_3$.

In a preferred embodiment, the silicon ion source is a silicon-containing hydroxyapatite having a Ca/P ratio in the range 2.05 to 2.55 and a Ca/(P+Si) molar ratio less than 1.66. Materials of this type are described in PCT/GB2009/002954.

Soaking such a silicon-containing hydroxyapatite in a cell culture medium (0.5 g/50 ml) was shown to release 17 ppm of silicon ions after 1 hour of soaking. Soaking an appropriate quantity of such a material in water for an appropriate period of time will lead to a solution containing a desired concentration of silicon ions due to release from the material. This silicon-ion-containing water can then be used to make up the gel solution by adding the desired polymer (for example, carboxymethyl cellulose). The solid inorganic component (synthetic bone graft material), in the form of, for example, granules or powder, can then be mixed with either the gel solution (if added before gelation) or with the resulting gel (if added after gelation).

In some embodiments of the present invention, the silicon ion source is selected from $Na_2SiO_3$ and a silicate-substituted calcium phosphate hydroxyapatite having a Ca/P ratio in the range 2.05 to 2.55 and a Ca/(P+Si) molar ratio less than 1.66 of the type described in PCT/GB2009/002954. The solid inorganic component may be independently selected from hydroxyapatite and a silicate-substituted calcium phosphate hydroxyapatite having a Ca/P ratio in the range 2.05 to 2.55 and a Ca/(P+Si) molar ratio less than 1.66 of the type described in PCT/GB2009/002954.

Pre-Pack

Another aspect of the present invention provides a bone graft pre-pack comprising (i) a solid inorganic component, which is a bone graft material; (ii) a dehydrated hydrogel; and (iii) an aqueous solution containing >2 ppm of silicon ions.

The solid inorganic component (e.g. a synthetic bone graft), the dehydrated hydrogel (e.g. lyophilised/freeze-dried carboxymethyl cellulose-containing hydrogel) and the aqueous solution mix to form a bone graft delivery system which comprises the solid inorganic component and a hydrogel containing silicon ions at the desired levels. As described above, those ions are then released during degradation of the hydrogel in vivo.

In this method, the lyophilising/freeze-drying is performed on a hydrogel which does not contain silicon ions. Such a hydrogel may or may not contain the solid inorganic component. The dry component then includes the solid inorganic component and the polymer (e.g. carboxymethyl cellulose) of the hydrogel, adhered to the particles (e.g. granules) of the solid inorganic component if that was present in the hydrogel. This freeze-dried component can be sterilised using standard industry methods such as gamma irradiation. It can then be rehydrated using an appropriate volume of an aqueous solution such as sterile water, sterile saline solution or bone marrow aspirate that contains silicon ions, for example a 100 ppm silicon-ion-containing solution as described in Example 7.

Alternatively, the lyophilising/freeze-drying is performed on a silicon-containing bone graft system as described above, leaving the polymer component (e.g. carboxymethyl cellulose) of the hydrogel and silicon ions adhered to the particles (e.g. granules) of the solid inorganic component. That is, the dry component includes the solid inorganic component, the polymer of the hydrogel, and the silicon ions of the hydrogel. This freeze-dried component can be sterilised using standard industry methods such as gamma irradiation. It can then be rehydrated using an appropriate volume of an aqueous solution such as sterile water, sterile saline solution or bone marrow aspirate.

Accordingly, a further aspect of the present invention therefore provides a bone graft pre-pack comprising (i) a solid inorganic component, which is a bone graft material; (ii) a dehydrated hydrogel containing an amount of silicon ions; and (iii) an aqueous solution; wherein the amount of silicon ions in the dehydrated hydrogel is such that on mixing with the aqueous solution a hydrogel is formed which contains >2 ppm of silicon ions, calculated as parts by weight of Si per million of the aqueous component of the hydrogel.

Such a pre-packs allow the desired bone graft system to be generated at a time and place suitable to the user, by mixing these components.

All features, including optional and preferred features, of the bone graft system of the invention described above are applicable as appropriate in the bone graft pre-pack of the invention also.

A further aspect of the present invention therefore provides a method of making a bone graft system from a bone graft pre-pack as described above, comprising the step of mixing components (i), (ii) and (iii).

In each of the methods described above, only the incorporation of silicon ions has been discussed explicitly. However, as described herein, the hydrogel may include other components, for example calcium or phosphate ions. These may be incorporated into the bone graft system using similar methods to those described above, such as soaking a calcium releasing component in an aqueous solution, or by mixing.

EMBODIMENTS OF THE INVENTION AND EXPERIMENTAL DATA

The present invention is now illustrated with reference to the following non-limiting examples and accompanying figures.

Example 1

Hydroxyapatite-Carboxymethyl Cellulose Gel Containing Silicon Ions

Crystalline sodium silicate ($Na_2SiO_3$) powder (0.218 g, which corresponds to 0.05 g silicon) was dissolved in 50 ml of deionised water (resulting in a solution containing 1000 ppm silicon ions). The pH was measured and adjusted to 7-7.8 by adding 1M HCl solution as needed. To the resulting solution, 2.5 g (5 wt %) of carboxymethyl cellulose (CMC, sodium salt, high viscosity) was added and the mixture was stirred and heated at 50° C. until the CMC had dissolved. 5 ml of this hydrogel solution was then mixed with 15 ml of porous (75% total porosity) hydroxyapatite ($Ca_{10}(PO_4)_6(OH)_2$) granules (1-2 mm diameter) and then cooled to room temperature to undergo gelation to form a synthetic bone graft substitute-organic polymer carrier system consisting of hydroxyapatite granules and CMC hydrogel. This bone graft system was stored in a sealed container until further use. This hydroxyapatite-CMC gel containing silicon ions can be sterilised using standard industry methods such as gamma irradiation.

Example 2

Hydroxyapatite

Collagen Gel Containing Silicon Ions

Crystalline sodium silicate ($Na_2SiO_3$) powder (0.218 g, which corresponds to 0.05 g silicon) was dissolved in 25 ml of deionised water (resulting in a solution containing 2000 ppm silicon ions). The pH was measured and adjusted to 7-7.8 by adding 1M HCl solution as needed. To 25 ml of 0.5M acetic acid, acid soluble bovine collagen type 1 (1 g, 4 wt %) was added and dissolved. This solution was mixed with the 25 ml silicon ion solution to produce a 2 wt % collagen solution containing 1000 ppm silicon ions. The pH of the mixture was adjusted to pH of approximately 7.4 using 1M NaOH. 5 ml of this hydrogel solution was then mixed with 15 ml of porous (75% total porosity) hydroxyapatite ($Ca_{10}(PO_4)_6(OH)_2$) granules (1-2 mm diameter) to form a synthetic bone graft substitute-organic polymer carrier system consisting of hydroxyapatite granules and collagen hydrogel solution, and this was aged at 37° C. overnight until gelation occurred. This bone graft system was stored in a sealed container until further use. This hydroxyapatite-collagen gel containing silicon ions can be sterilised using standard industry methods such as gamma irradiation.

Example 3

Hydroxyapatite

Pluronic® Gel Containing Silicon Ions

Crystalline sodium silicate ($Na_2SiO_3$) powder (0.218 g, which corresponds to 0.05 g silicon) was dissolved in 50 ml of deionised water (resulting in a solution containing 1000 ppm silicon ions). The pH was measured and adjusted to 7-7.8 by adding 1M HCl solution as needed. This solution was cooled to 4° C. and Pluronic® F-127 (10 g, 20 wt %) was added. The solution stirred overnight at 4° C. to dissolve the Pluronic® polymer. 5 ml of this hydrogel solution was then mixed with 15 ml of porous (75% total porosity) hydroxyapatite ($Ca_{10}(PO_4)_6(OH)_2$) granules (1-2 mm diameter) to form a synthetic bone graft substitute-organic polymer carrier system consisting of hydroxyapatite granules and Pluronic® hydrogel solution, and this mixture was warmed to 37° C. overnight to allow gelation to occur. This bone graft system was stored in a sealed container until further use. This hydroxyapatite-Pluronic® gel containing silicon ions can be sterilised using standard industry methods such as gamma irradiation.

Example 4

Biphasic Calcium Phosphate

Carboxymethyl Cellulose Gel Containing Silicon Ions

Crystalline sodium silicate ($Na_2SiO_3$) powder (0.218 g, which corresponds to 0.05 g silicon) was dissolved in 50 ml of deionised water (resulting in a solution containing 1000 ppm silicon ions). The pH was measured and adjusted to 7-7.8 by adding 1M HCl solution as needed. To the resulting solution, 2.5 g (5 wt %) of carboxymethyl cellulose (CMC, sodium salt, high viscosity) was added and the mixture was stirred and heated at 50° C. until the CMC had dissolved. 5 ml of this hydrogel solution was then mixed with 15 ml of porous (75% total porosity) biphasic calcium phosphate (50% hydroxyapatite ($Ca_{10}(PO_4)_6(OH)_2$); 50% β-tricalcium phosphate ($Ca_3(PO_4)_2$)) granules (1-2 mm diameter) and then cooled to room temperature to undergo gelation to form a synthetic bone graft substitute-organic polymer carrier system consisting of biphasic calcium phosphate granules and CMC hydrogel. This bone graft system was stored in a sealed container until further use. This biphasic calcium phosphate-CMC gel containing silicon ions can be sterilised using standard industry methods such as gamma irradiation.

Example 5

Biphasic Calcium Phosphate

Collagen Gel Containing Silicon Ions

Crystalline sodium silicate ($Na_2SiO_3$) powder (0.218 g, which corresponds to 0.05 g silicon) was dissolved in 25 ml of deionised water (resulting in a solution containing 2000 ppm silicon ions). The pH was measured and adjusted to 7-7.8 by adding 1M HCl solution as needed. To 25 ml of 0.5M acetic acid, acid soluble bovine collagen type 1 (1 g, 4 wt %) was added and dissolved. This solution was mixed with the 25 ml silicon ion solution to produce a 2 wt % collagen solution containing 1000 ppm silicon ions. The pH of the mixture was adjusted to pH of approximately 7.4 using 1M NaOH. 5 ml of this hydrogel solution was then mixed with 15 ml of porous (75% total porosity) biphasic calcium phosphate (50% hydroxyapatite ($Ca_{10}(PO_4)_6(OH)$ $_2$); 50% β-tricalcium phosphate (Ca$_3$(PO$_4$)$_2$)) granules (1-2 mm diameter) to form a synthetic bone graft substitute-organic polymer carrier system consisting of biphasic calcium phosphate granules and collagen hydrogel solution, and this was aged at 37° C. overnight until gelation occurred. This bone graft system was stored in a sealed container until further use. This biphasic calcium phosphate-collagen gel containing silicon ions can be sterilised using standard industry methods such as gamma irradiation.

Example 6

Biphasic Calcium Phosphate

Pluronic® Gel Containing Silicon Ions

Crystalline sodium silicate (Na$_2$SiO$_3$) powder (0.218 g, which corresponds to 0.05 g silicon) was dissolved in 50 ml of deionised water (resulting in a solution containing 1000 ppm silicon ions). The pH was measured and adjusted to 7-7.8 by adding 1M HCl solution as needed. This solution was cooled to 4° C. and Pluronic® F-127 (10 g, 20 wt %) was added. The solution stirred overnight at 4° C. to dissolve the Pluronic® polymer. 5 ml of this hydrogel solution was then mixed with 15 ml of porous (75% total porosity) biphasic calcium phosphate (50% hydroxyapatite (Ca$_{10}$(PO$_4$)$_6$(OH)$_2$); 50% β-tricalcium phosphate (Ca$_3$(PO$_4$)$_2$)) granules (1-2 mm diameter) to form a synthetic bone graft substitute-organic polymer carrier system consisting of biphasic calcium phosphate granules and Pluronic® hydrogel solution, and this mixture was warmed to 37° C. overnight to allow gelation to occur. This bone graft system was stored in a sealed container until further use. This biphasic calcium phosphate-Pluronic® gel containing silicon ions can be sterilised using standard industry methods such as gamma irradiation.

Example 7

Silicon-Containing Hydroxyapatite

CMC Gel Containing Silicon Ions

Crystalline sodium silicate (Na$_2$SiO$_3$) powder (0.218 g, which corresponds to 0.05 g silicon) was dissolved in 50 ml of deionised water (resulting in a solution containing 1000 ppm silicon ions). The pH was measured and adjusted to 7-7.8 by adding 1M HCl solution as needed. To this solution, 2.5 g (5 wt %) of carboxymethyl cellulose (CMC, sodium salt, high viscosity) was added and the mixture was stirred and heated at 50° C. until the CMC has dissolved. 5 ml of this hydrogel solution was then mixed with 15 ml of porous (75% total porosity) silicon-containing hydroxyapatite (Ca$_{9.85}$(PO$_4$)$_4$(SiO$_4$)$_2$(OH)$_y$) granules (1-2 mm diameter, containing approximately 5.2 wt % silicon ions) and then cooled to room temperature to undergo gelation to form a synthetic bone graft substitute-organic polymer carrier system consisting of silicon-containing hydroxyapatite granules and CMC hydrogel. This bone graft system was stored in a sealed container until further use. This silicon-containing hydroxyapatite-CMC gel containing silicon ions can be sterilised using standard industry methods such as gamma irradiation.

Example 8

Silicon-Containing Hydroxyapatite

Collagen Gel Containing Silicon Ions

Crystalline sodium silicate (Na$_2$SiO$_3$) powder (0.218 g, which corresponds to 0.05 g silicon) was dissolved in 25 ml of deionised water (resulting in a solution containing 2000 ppm silicon ions). The pH was measured and adjusted to 7-7.8 by adding 1M HCl solution as needed. To 25 ml of 0.5M acetic acid, acid soluble bovine collagen type 1 (1 g, 4 wt %) was added and dissolved. This solution was mixed with the 25 ml silicon ion solution to produce a 2 wt % collagen solution containing 1000 ppm silicon ions. The pH of the mixture was adjusted to pH of approximately 7.4 using 1M NaOH. 5 ml of this hydrogel solution was then mixed with 15 ml of porous (75% total porosity) silicon-containing hydroxyapatite (Ca$_{9.85}$(PO$_4$)$_4$(SiO$_4$)$_2$(OH)$_y$) granules (1-2 mm diameter, containing approximately 5.2 wt % silicon ions) to form a synthetic bone graft substitute-organic polymer carrier system consisting of silicon-containing hydroxyapatite granules and collagen hydrogel solution, and this was aged at 37° C. overnight until gelation occurred. This bone graft system was stored in a sealed container until further use. This silicon-containing hydroxyapatite-collagen gel containing silicon ions can be sterilised using standard industry methods such as gamma irradiation.

Example 9

Silicon-Containing Hydroxyapatite

Pluronic® Gel Containing Silicon Ions

Crystalline sodium silicate (Na$_2$SiO$_3$) powder (0.218 g, which corresponds to 0.05 g silicon) was dissolved in 50 ml of deionised water (resulting in a solution containing 1000 ppm silicon ions) The pH was measured and adjusted to 7-7.8 by adding 1M HCl solution as needed. This solution was cooled to 4° C. and Pluronic® F-127 (10 g, 20 wt %) was added. The solution stirred overnight at 40° C. to dissolve the Pluronic® polymer. 5 ml of this hydrogel solution was then mixed with 15 ml of porous (75% total porosity) silicon-containing hydroxyapatite (Ca$_{9.85}$(PO$_4$)$_4$(SiO$_4$)$_2$(OH)$_y$) granules (1-2 mm diameter, containing approximately 5.2 wt % silicon ions) to form a synthetic bone graft substitute-organic polymer carrier system consisting of silicon-containing hydroxyapatite granules and Pluronic® hydrogel solution, and this mixture was warmed to 37° C. overnight to allow gelation to occur. This bone graft system was stored in a sealed container until further use. This silicon-containing hydroxyapatite-Pluronic® gel containing silicon ions can be sterilised using standard industry methods such as gamma irradiation.

Example 10

Silicon-Containing Hydroxyapatite

CMC-Glycerol Gel Containing Silicon Ions

Crystalline sodium silicate (Na$_2$SiO$_3$) powder (0.218 g, which corresponds to 0.05 g silicon) was dissolved in 50 ml of deionised water (resulting in a solution containing 1000 ppm silicon ions). The pH was measured and adjusted to 7-7.8 by adding 1M HCl solution as needed. To this solution, 2.5 g (5 wt %) of carboxymethyl cellulose (CMC, sodium salt, high viscosity) and 5 g glycerol were added and the mixture was stirred and heated at 50° C. until the CMC has dissolved. 5 ml of this hydrogel solution was then mixed with 15 ml of porous (75% total porosity) silicon-containing hydroxyapatite ($Ca_{9.85}(PO_4)_4(SiO_4)_2(OH)_y$) granules (1-2 mm diameter, containing approximately 5.2 wt % silicon ions) and then cooled to room temperature to undergo gelation to form a synthetic bone graft substitute-organic polymer carrier system consisting of silicon-containing hydroxyapatite granules and CMC-glycerol hydrogel. This bone graft system was stored in a sealed container until further use. This silicon-containing hydroxyapatite-CMC-glycerol gel containing silicon ions can be sterilised using standard industry methods such as gamma irradiation.

Example 11

Bone Graft Gels Containing Various Silicon Ion Concentrations

By further example a range of silicon-containing solutions were prepared to make gel solutions as described in any of examples 1-10. Amounts of crystalline sodium silicate ($Na_2SiO_3$) powder as described in Table 1 were used to produce a range of concentrations of silicon-containing solutions. Each quantity in Table 1 was added to 50 ml of deionised water to produce solutions with final concentrations of 5, 10, 50, 100, 250, 500, 1000 and 2000 ppm of silicon ions. For each solution the pH was measured and adjusted to 7-7.8 by adding 1M HCl solution as needed. These solutions were then used to make synthetic bone graft substitute-organic polymer carrier systems as described in Examples 1-9.

TABLE 1

| Amount of $Na_2SiO_3$ powder (g) | Equivalent amount of Si (g) | Final concentration of silicon ions in 50 ml water (ppm) |
| --- | --- | --- |
| 0.0011 | 0.00025 | 5 |
| 0.0022 | 0.0005 | 10 |
| 0.011 | 0.0025 | 50 |
| 0.022 | 0.005 | 100 |
| 0.0545 | 0.0125 | 250 |
| 0.109 | 0.025 | 500 |
| 0.218 | 0.05 | 1000 |
| 0.436 | 0.10 | 2000 |

Table 1 shows the quantities of $Na_2SiO_3$ powder (g) to be added to 50 ml of deionised water to produce silicon-ion-containing solutions with silicon ion concentrations of 5, 10, 50, 100, 250, 500, 1000 and 2000 ppm.

Example 12

Hydroxyapatite

CMC Gel Containing Silicon Ions from a Silicon-Containing Hydroxyapatite

A silicon-containing hydroxyapatite ($Ca_{9.85}(PO_4)_4(SiO_4)_2(OH)_y$) as described in PCT/GB2009/002954 in the form of a powder (particle size between 75 and 212 µm) was soaked in deionised water (0.5 g/50 ml) for 1 hour, releasing approximately 20 ppm silicon ions into the water. The pH of the solution was measured and adjusted to 7-7.8 by adding 1M HCl solution as needed. To this solution, 2.5 g (5 wt %) of carboxymethyl cellulose (CMC, sodium salt, high viscosity) was added and the mixture was stirred and heated at 50° C. until the CMC had dissolved. 5 ml of this hydrogel solution was then mixed with 15 ml of porous (75% total porosity) hydroxyapatite ($Ca_{10}(PO_4)_6(OH)_2$) granules (1-2 mm diameter) and then cooled to room temperature to undergo gelation to form a synthetic bone graft substitute-organic polymer carrier system consisting of hydroxyapatite granules and CMC hydrogel. This bone graft system was stored in a sealed container until further use. This hydroxyapatite-CMC gel containing silicon ions can be sterilised using standard industry methods such as gamma irradiation. This method could also be used to make bone graft systems with collagen and Pluronics® as described in Examples 2, 3, 5, 6, 8 and 9.

Example 13

Silicon-Containing Hydroxyapatite

CMC Gel Containing Silicon Ions from a Silicon-Containing Hydroxyapatite

A silicon-containing hydroxyapatite ($Ca_{9.85}(PO_4)_4(SiO_4)_2(OH)_y$) as described in PCT/GB2009/002954 in the form of a powder (particle size between 75 and 212 µm) was soaked in deionised water (0.5 g/50 ml) for 1 hour, releasing approximately 20 ppm silicon ions into the water. The pH of the solution was measured and adjusted to 7-7.8 by adding 1M HCl solution as needed. To this solution, 2.5 g (5 wt %) of carboxymethyl cellulose (CMC, sodium salt, high viscosity) was added and the mixture was stirred and heated at 50° C. until the CMC had dissolved. 5 ml of this hydrogel solution was then mixed with 15 ml of porous (75% total porosity) silicon-containing hydroxyapatite ($Ca_{9.85}(PO_4)_4(SiO_4)_2(OH)_y$) granules (1-2 mm diameter, containing approximately 5.2 wt % silicon ions) and then cooled to room temperature to undergo gelation to form a synthetic bone graft substitute-organic polymer carrier system consisting of silicon-containing hydroxyapatite granules and CMC hydrogel. This bone graft system was stored in a sealed container until further use. This silicon-containing hydroxyapatite—CMC gel containing silicon ions can be sterilised using standard industry methods such as gamma irradiation. This method could also be used to make bone graft systems with collagen and Pluronics® as described in Examples 2, 3, 5, 6, 8 and 9.

Example 14

Silicon-Containing Hydroxyapatite

CMC Gel 2.5 g (5 wt %) of Carboxymethyl cellulose (CMC, sodium salt, high viscosity) was added to 50 ml of deionised water and the mixture was stirred and heated at 50° C. until the CMC had dissolved. 5 ml of this hydrogel solution was then mixed with 15 ml of porous (75% total porosity) silicon-containing hydroxyapatite ($Ca_{9.85}(PO_4)_4(SiO_4)_2(OH)_y$) granules (1-2 mm diameter, containing approximately 5.2 wt % silicon ions) for 1.5 minutes and then cooled to room temperature to undergo gelation to form a synthetic bone graft substitute-organic polymer carrier system consisting of silicon-containing hydroxyapatite granules and CMC hydrogel. Silicon ions were released from the granules into the hydrogel. This bone graft system was stored in a sealed container until further use. This silicon-containing hydroxyapatite-CMC gel can be sterilised using standard industry methods such as gamma irradiation.

Example 15

Silicon-Containing Hydroxyapatite

CMC Gel 2.5 g (5 wt %) of carboxymethyl cellulose (CMC, sodium salt, high viscosity) was added to 50 ml of deionised water and the mixture was stirred and heated at 50° C. until the CMC had dissolved. 5 ml of this gel solution was then mixed with 15 ml of porous (75% total porosity) silicon-containing hydroxyapatite ($Ca_{9.85}(P_4)_4(SiO_4)_2(OH)_y$) granules (1-2 mm diameter, containing approximately 5.2 wt % silicon ions) for 12 hours and then cooled to room temperature to undergo gelation to form a synthetic bone graft substitute-organic polymer carrier system consisting of silicon-con-containing hydroxyapatite granules and CMC hydrogel. Silicon ions were released from the granules into the hydrogel and the prolonged mixing time of 12 hours increased the amount of silicon ions released from the granules into the hydrogel compared to Example 14. This bone graft system was stored in a sealed container until further use. This silicon-containing hydroxyapatite-CMC gel can be sterilised using standard industry methods such as gamma irradiation.

Example 16

Lyophilised/Freeze Dried Silicon-Containing Hydroxyapatite

CMC Gel

A synthetic bone graft substitute-organic polymer carrier system consisting of silicon-containing hydroxyapatite granules and CMC hydrogel as described in Example 7, Example 10, or any one of Examples 13 to 15 can be lyophilised/freeze dried to remove the water from the hydrogel, leaving CMC and silicon ions adhered to the granules. This lyophilised/freeze dried silicon-containing hydroxyapatite-CMC gel can be sterilised using standard industry methods such as gamma irradiation. This can then be re-hydrated using an appropriate volume of an aqueous solution such as sterile water, sterile saline solution or bone marrow aspirate.

Example 17

Lyophilised/Freeze Dried Synthetic Bone Graft

CMC Gel, Rehydrated Using Silicon-Ion-Containing Solution

A synthetic bone graft substitute-organic polymer carrier system consisting of synthetic bone graft granules and CMC hydrogel as described in any one of Examples 1, 4, 7, 10, or 12 to 15 could be lyophilised/freeze dried to remove the water from the hydrogel, leaving CMC adhered to the granules. This lyophilised/freeze dried silicon-containing hydroxyapatite-CMC gel can be sterilised using standard industry methods such as gamma irradiation. This can then be re-hydrated using an appropriate volume of an aqueous solution such as sterile water, sterile saline solution or bone marrow aspirate that contain silicon ions, such as a 200 ppm silicon ion-containing solution as described in Example 11.

Example 18

Lyophilised/Freeze Dried Silicon-Containing Hydroxyapatite

Collagen Gel

A synthetic bone graft substitute-organic polymer carrier system consisting of silicon-containing hydroxyapatite granules and collagen hydrogel as described in Example 8, or alternatively derived using the methods described for CMC hydrogels in Examples 13 to 15 could be lyophilised/freeze dried to remove the water from the hydrogel, leaving collagen and silicon ions adhered to the granules. This lyophilised/freeze dried silicon-containing hydroxyapatite-collagen gel can be sterilised using standard industry methods such as gamma irradiation. This can then be re-hydrated using an appropriate volume of an aqueous solution such as sterile water, sterile saline solution or bone marrow aspirate.

Example 19

Lyophilised/Freeze Dried Synthetic Bone Graft

Collagen Gel, Rehydrated Using Silicon-Ion-Containing Solution

A synthetic bone graft substitute-organic polymer carrier system consisting of synthetic bone graft granules and collagen hydrogel as described in any one of Examples 2, or 8, or alternatively derived using the methods described for CMC hydrogels in Examples 12 to 15 could be lyophilised/freeze dried to remove the water from the gel, leaving collagen adhered to the granules. This lyophilised/freeze dried synthetic bone graft-collagen gel can be sterilised using standard industry methods such as gamma irradiation. This can then be re-hydrated using an appropriate volume of an aqueous solution such as sterile water, sterile saline solution or bone marrow aspirate that contain silicon ions, such as a 200 ppm silicon ion-containing solution as described in Example 11.

The invention claimed is:

1. A bone graft system comprising
a solid inorganic component, which is bone graft material; and
a hydrogel,
wherein the hydrogel contains greater than or equal to 5 ppm and less than or equal to 1000 ppm of silicate ions dissolved within the aqueous component of the hydrogel, calculated as parts by weight of Si per million of the aqueous component of the hydrogel.

2. A bone graft system according to claim 1, wherein the ratio by volume of the solid inorganic component to the hydrogel is between 90:10 and 50:50.

3. A bone graft system according to claim 1, wherein the solid inorganic component is in the form of granules of diameter between 0.1 and 5 mm.

4. A bone graft system according to claim 1, wherein the solid inorganic component comprises hydroxyapatite or a silicon-containing hydroxyapatite.

5. A bone graft system according to claim 4, wherein the solid inorganic component comprises a silicon-containing hydroxyapatite having a Ca/P ratio in the range 2.05 to 2.55 and a Ca/(P+Si) molar ratio less than 1.66.

6. A bone graft system according to claim 4 or claim 5, wherein the solid inorganic component comprises a silicon-containing hydroxyapatite, the silicon atom content of which is in the range of 2.9 to 6 wt %.

7. A bone graft system according to claim 4 or 5, wherein the solid inorganic component comprises a compound represented by formula (I):

$$Ca_{10-\delta}(PO_4)_{6-x}(SiO_4)_x(OH)_{2-x} \quad (I)$$

wherein $1.1 \leq x \leq 2.0$, and $\delta$ represents a Ca deficiency such that the Ca/(P+Si) molar ratio has a value less than 1.667.

8. A bone graft system according to claim 7, wherein $1.6 \leq x \leq 2.0$.

9. A bone graft system according to claim 1, 4 or 5, wherein the solid inorganic component comprises a compound of the formula $XO-Y_2O-SiO_2$ or $XO-Y_2O-SiO_2-P_2O_5$, wherein each X is independently selected from the group consisting of Ca, Mg and Sr, and each Y is independently selected from the group consisting of Na and K.

10. A bone graft system according to claim 1, 4 or 5, wherein the hydrogel comprises carboxymethyl cellulose, collagen, or an ethylene oxide/propylene oxide block copolymer.

11. A bone graft system according to claim 1, 4 or 5, wherein the hydrogel further contains calcium ions.

12. A bone graft system according to claim 1, 4 or 5, wherein the hydrogel further contains phosphate ions.

13. A bone graft system according to claim 1, 4 or 5, wherein the hydrogel further contains ions of one or more elements selected from strontium, magnesium, potassium, copper, cobalt, nickel, zinc, selenium, silver and fluorine.

14. A method of making a bone graft system according to claim 1, 4 or 5, comprising the step of mixing a silicate ion source with a hydrogel to form a hydrogel containing greater than or equal to 5 ppm and less than or equal to 1000 ppm of silicate ions, calculated as parts by weight of Si per million of the aqueous component of the hydrogel, and further comprising the step of mixing a solid inorganic component, which is a bone graft material, with the hydrogel.

15. A method according to claim 14, wherein the silicate ion source is selected from the group consisting of:
(i) sodium silicates;
(ii) calcium silicates;
(iii) compounds of the formula $XO-Y_2O-SiO_2$ or $XO-Y_2O-SiO_2-P_2O_5$, wherein each X is independently selected from the group consisting of Ca, Mg and Sr, and each Y is independently selected from the group consisting of Na and K; and
(iv) hydroxyapatites.

16. A method according to claim 15, wherein the silicate ion source is selected from $Na_4SiO_4$, $Na_2SiO_3$, $Na_2Si_2O_5$, $Na_2Si_3O_7$, hydrated forms of these sodium silicates, and amorphous compositions of sodium silicate.

17. A method according to claim 16, wherein the silicate ion source is $Na_2SiO_3$.

18. A method according to claim 15, wherein the silicate ion source is selected from $CaSiO_3$ (wollastonite) and amorphous calcium silicate glass compositions in the $CaO-SiO_2$ system.

19. A method according to claim 15, wherein the silicate ion source is a silicon-containing hydroxyapatite having a Ca/P ratio in the range 2.05 to 2.55 and a Ca/(P+Si) molar ratio less than 1.66.

20. A method of making a bone graft system according to claim 1, 4 or 5, comprising the steps of
(a) soaking or dissolving a suitable silicon-containing bone graft material in an aqueous solution to form a solution comprising greater than or equal to 5 ppm and less than or equal to 1000 ppm of silicate ions;
(b) mixing the resulting aqueous solution with a polymer to form a gel solution;
(c) allowing gelation of the gel solution to occur to form a hydrogel; and
(d) mixing a solid inorganic component with the resulting hydrogel to make up the bone graft system.

21. A method of making a bone graft system according to claim 1, 4 or 5 comprising the steps of
(a) soaking or dissolving a suitable silicate ion source in an aqueous solution to form a solution comprising greater than or equal to 5 ppm and less than or equal to 1000 ppm of silicate ions;
(b) mixing the resulting aqueous solution with a polymer to form a gel solution;
(c) mixing a solid inorganic component with the gel solution; and
(d) allowing gelation of the gel solution to occur to form the bone graft system.

22. A bone graft pre-pack comprising
(i) a solid inorganic component, which is a bone graft material;
(ii) a dehydrated hydrogel containing an amount of silicate ions; and
(iii) an aqueous solution;
wherein the amount of silicate ions in the dehydrated hydrogel is such that on mixing with the aqueous solution a hydrogel is formed which contains greater than or equal to 5 ppm and less than or equal to 1000 ppm of silicate ions, calculated as parts by weight of Si per million of the aqueous component of the hydrogel.

* * * * *